Figure 1:
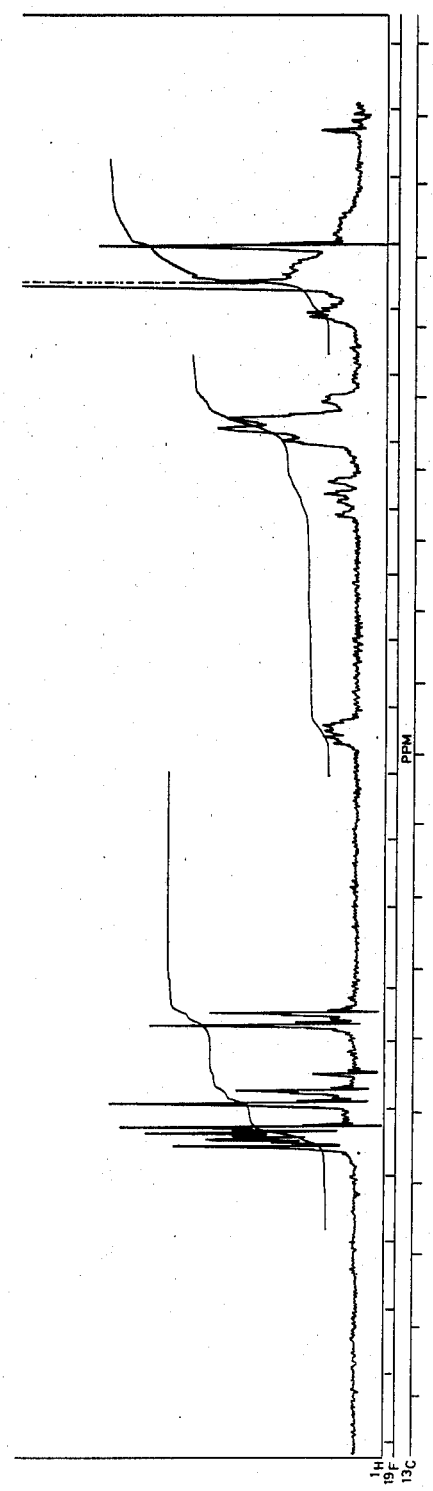

United States Patent [19]

Reiner

[11] 4,355,166
[45] Oct. 19, 1982

[54] QUINUCLIDINIC ESTER AND DERIVATIVES OF PHENOXYCARBOXYLIC ACIDS

[75] Inventor: Alberto Reiner, Como, Italy

[73] Assignee: D and D S.r.l., Milan, Italy

[21] Appl. No.: 245,273

[22] Filed: Mar. 19, 1981

[30] Foreign Application Priority Data

Mar. 19, 1980 [IT] Italy .............................. 20764 A/80

[51] Int. Cl.³ .................. C07D 473/08; C07D 453/02
[52] U.S. Cl. .................................. 544/268; 424/253; 424/263; 424/266; 424/267; 546/137
[58] Field of Search ...................... 546/137; 544/268; 424/263, 266, 267, 253

[56] References Cited

PUBLICATIONS

March, J., *Advanced Organic Chemistry*, McGraw Hill, New York, 1968, pp. 319–320.
Chemical Abstracts, 88: 37424j, (1978), [German Ols 2,713,596, Lafon, 10/13/77].
Mashkovsky, M., in *Proc. Ist. Int. Pharm. Meeting*, vol. 7, (Brunings, editor), Pergamon Press, Oxford, 1963, pp. 359–366.
Chemical Abstracts, 79: 53029d, (1973), [German Ols 2,250,327, Mieville, 4/26/73].

*Primary Examiner*—Richard A. Schwartz
*Attorney, Agent, or Firm*—Murray and Whisenhunt

[57] ABSTRACT

The invention relates to esters of 3-hydroxy-quinuclidine with phenoxycarboxylic acids, and their salts having general formula:

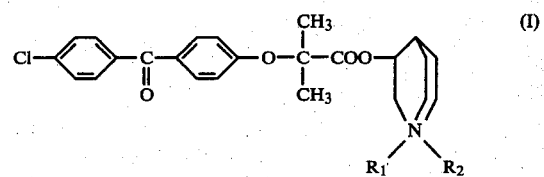

wherein $R_1$ represents H, $CH_3$, and $R_2$ represents H, Cl, Br or a radical of an acid of the group comprising oleic, pivalic, nicotinic, clofibric, pyridineacetic and teophyllineacetic acid.

The compounds of the invention jointly show hypocholesteremizing and hypotriglyceridimizing activity, combined with other therapeutically interesting properties, such as beta-blocking, diuretic, anti-inflammatory activity.

The invention furthermore relates to the pharmaceutical compositions containing the compounds of the invention as the active ingredients.

10 Claims, 2 Drawing Figures

QUINUCLIDINIC ESTER AND DERIVATIVES OF PHENOXYCARBOXYLIC ACIDS

The present invention relates to esters and derivatives of 3-hydroxy-quinuclidine with phenoxycarboxylic acids, having general formula:

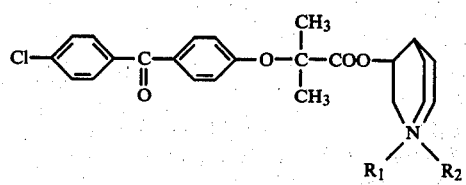 (I)

wherein $R_1$ represents H, $CH_3$, and $R_2$ represents H, Cl Br, or a radical of an acid of the group comprising oleic, pivalic, nicotinic, clofibric, pyridineacetic and teophyllineacetic acid.

In fact, it has been found that the compounds of the invention are endowed with the joint properties of hypocholesteremizing and hypotriglyceridimizing activity, in combination with other therapeutically interesting properties, such as beta-blocking, diuretic, anti-inflammatory activity.

The anti-cholesteremic and anti-lypemic activity is known of the derivatives of phenoxycarboxylic acids, having the general formula:

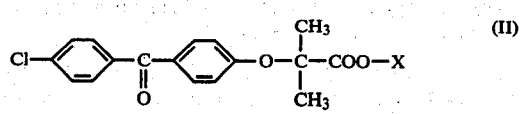 (II)

amongst which the isopropyl-p-(4-carbobenzoyl)-phenoxy-isobutyrate, having the formula:

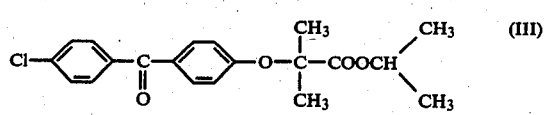 (III)

also known under the generic name "Procetofene", is mainly used. The 3-hydroxy-quinuclidine, in turn, is a known substance, theoretically having hypotensive action, although it has not found direct therapeutical use.

On the basis of the preceding considerations, however, nothing might lead to the supposition that esters and derivatives of 3-hydroxy-quinuclidine with p-(4-chlorobenzoyl)-phenoxy-isobutyric acid, (hereinafter also indicated as procetophene acid), might show the aforementioned activities in a remarkable manner. The process for the preparation of derivatives and esters according to the present invention comprises the following steps:

(a) chlorination of p-(4-chlorobenzoyl)-phenoxy-isobutyric acid with an excess chlorinating agent, preferably thionyl chloride or phosphorus pentachloride;

(b) reaction of the chloride of procetophene acid with 3-hydroxy-quinuclidine in an organic solvent, at the maximum temperature of 70° C., with the isolation of the ester, and (c) possible salt forming reaction with the desired acid, in an organic solvent, particularly acetone or ethyl alcohol.

The following example illustrates, without any limiting purpose, the process for the preparation of the compounds of the invention.

EXAMPLE 50 g of p-(4-chlorobenzoyl)-phenoxy-isobutyric acid are supplemented with 120 mls of thionyl chloride, a cream coloured paste being thus formed; the temperature of the paste is increased, by an external heating bath up to about 75° C. In order to control the reaction pattern, the gas development is monitored by means of a gas trap, until it ceases, which indicates the completion of the reaction (about 45 minutes). The reaction mixture is cooled and the excess of thionyl chloride is distilled; the residue, taken with benzol, is distilled again, giving place to a waxy crystalline product having a white-creamy colour.

48 g of the product, having m.p. of 80° C., are obtained by crystallization from hexane.

44 g of chloride of p-(4-chlorobenzoyl)-phenoxy-isobutyric acid, (10% excess), are charged in a flask containing 120 mls of pyridine, and then 15 g of 3-hydroxyquinuclidine are slowly added.

The reaction mixture becomes slightly and gradually heated and the reaction is completed within about 3 hours, the reaction temperature being controlled at a maximum value of about 70° C. At the end of the reaction the excess pyridine is distilled, leaving a dense oil, which is water soluble and gives place to a clear solution. The residue is taken with water and ammonia and then extracted three times with chloroform. The combined chloroformic extracts are washed with water, decanted and dried, the chloroform being thereafter distilled under vacuum. By further adding water, the oily residue is converted into a white cream-coloured solid, which is washed again to remove all the residual pyridine.

The product is dissolved in acetone (400 mls) and filtered through active carbon. The product is precipitated by diluting it with water (ratio 3:1), giving place to 40 g of 3-hydroxy-quinuclidine ester of p-(4-chlorobenzoyl)-phenoxy-isobutyric acid, which is crystalline and cream coloured.

For the preparation of the single salts of the ester, the latter is reacted, in the stechiometrical ratio, with the corresponding acids.

More specifically:

(a) Hydrochloride. The basic ester, (namely 3-hydroxy-quinuclidine ester of p-(4-chlorobenzoyl)-phenoxy-isobutyric acid), is dissolved in methylisobutylketone and gaseous hydrogen chloride is bubbled through the solution. The hydrochloride precipitates and is separated by filtration.

(b) Methylbromide. Methylbromide is absorbed in acetone until the saturation is achieved and this acetone solution is reacted with an acetone solution of the basic ester.

The other salts according to the present invention are likely prepared, provided that, in the case of oleate, pivalate and clofibrate, acetone is used as the solvent, and ethanol is used in the case of nicotinate, pyridineacetate and theophyllineacetate. Hereinafter the data of the single compounds of the invention are reported:

I  3-hydroxy-quinuclidine ester of p-(4-chlorobenzoyl)-phenoxy-isobutyric acid:

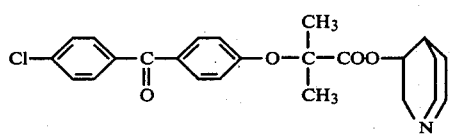

Molecular weight: 427.397. Melting point: 109°–111° C. Chromatographic analysis, (eluant: chloroform/methanol/ammonia: 40/8/1) a pure product, having a chemical titre of 99.8%, is found.

The product is not water soluble and crystallizes from cyclohexane.

Figure 2:
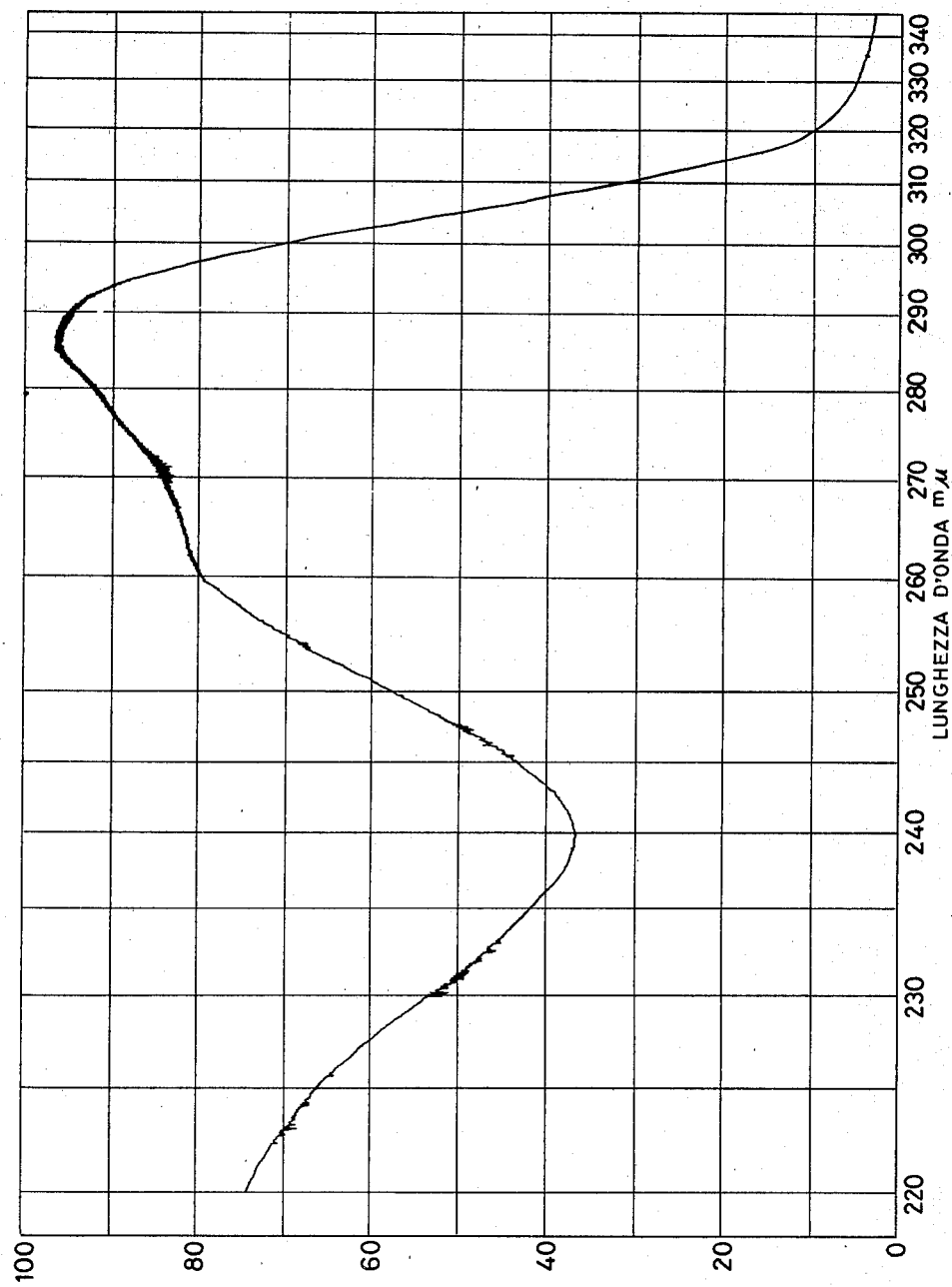

The NMR and UV spectra are respectively shown in FIGS. 1 and 2.

The analysis for $C_{24}H_{26}NO_4Cl$ gives: calculated: C% 67.36; H% 6.12; N% 3.27; Cl% 8.28: found: C% 67.10; H% 6.20; N% 3.05; Cl% 8.32.

II  3-hydroxy-quinuclidine ester of p-(4-chlorobenzoyl)-phenoxy-isobutyric acid hydrochloride

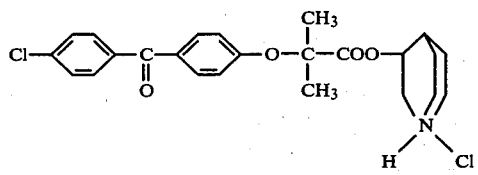

Molecular weight: 464.407. Melting point: 180°–183° C. By chromatographic analysis a pure product, having a chemical titre of 99%, is found.

The analysis for $C_{24}H_{27}NO_4Cl$ gives: calculated: C% 62.07; H% 5.86; N% 3.01; Cl% 15.26: found: C% 61.98%; H% 5.75; N% 3.18; Cl% 15.12.

III  3-hydroxy-quinuclidine ester of p-(4-chlorobenzoyl)-phenoxy-isobutyric acid oleate

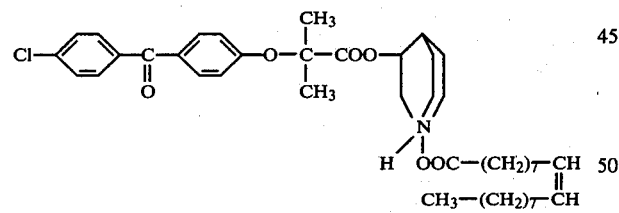

Molecular weight: 710.410. Melting point: dense oil (oily crystal).

By chromatographic analysis a pure product is found.

IV  3-hydroxy-quinuclidine ester of p-(4-chlorobenzoyl)-phenoxy-isobutyric acid methylbromide

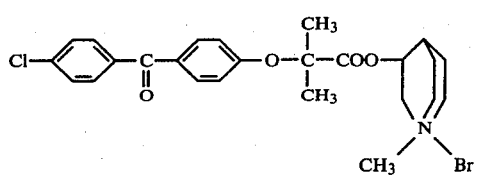

Molecular weight: 522.888. Melting point: 220°–221° C. By chromatographic analysis a pure product having a chemical titre of 98.8%, is found.

V  3-hydroxy-quinuclidine ester of p-(4-chlorobenzoyl)-phenoxy-isobutyric acid pivalate

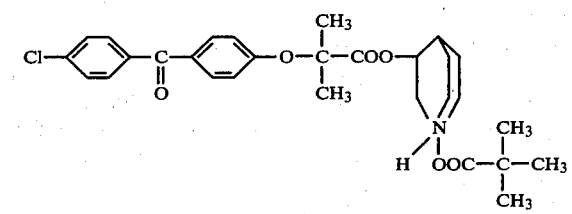

Molecular weight: 530.072. Melting point: dense oily, low melting product (about 82°–84° C.).

By cromatographic analysis a pure product, having a chemical titre of 99%, is found.

VI  3-hydroxy-quinuclidine ester of p-(4-chlorobenzoyl)-phenoxy-isobutyric acid nicotinate.

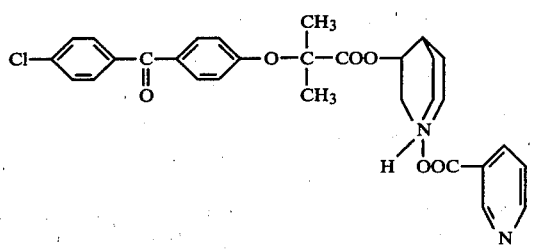

VII  3-hydroxy-quinuclidine ester of p-(4-chlorobenzoyl)-phenoxy-isobutyric acid clofibrate

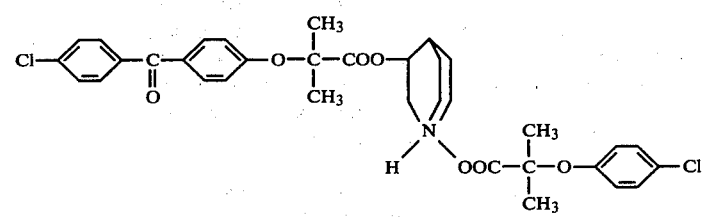

Molecular weight 642.592. Melting point: 101°–103° C. A pure product is found by chromatographic analysis.

VIII 3-hydroxy-quinuclidine ester of
p-(4-chlorobenzoyl)-phenoxy-isobutyric acid
pyridineacetate

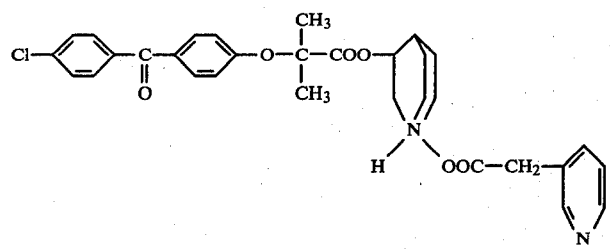

Molecular weight: 565.071. Melting point: 74°-76° C.
By chromatographic analysis a pure product is found.

IX 3-hydroxy-quinuclidine ester of
p-(4-chlorobenzoyl)-phenoxy-isobutyric acid
theophyllineacetate

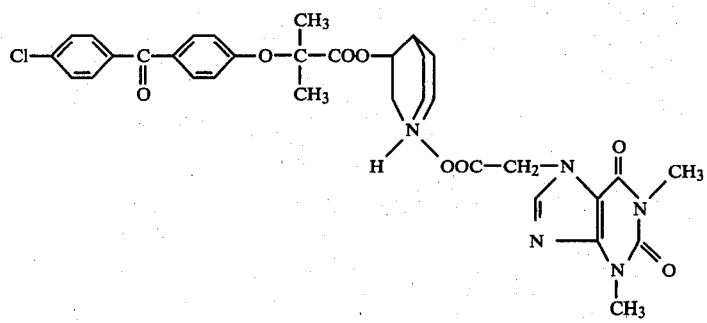

Molecular weight: 666.148.

The melting point can not be determined since the product is hygroscopic. The compounds of the invention were subjected to pharmacological tests, in which not only the pharmacological properties were assessed in absolute way, but also an evaluation in comparison with already known active substances was carried out. Particularly all the compounds showed a high hypocholesteremizing and hypotryglyceridimizing activity; in comparison with clofibrate, the compounds of the invention show, (the dosages being the same and by oral route,) a relevantly higher activity.

Of course, such a property is even more important, if account is taken of the modest toxicity of the compounds of the invention.

In most compounds of the invention, the aforesaid basic properties are accompanied by a blocking activity towards the beta-adrenergic receptors, such an activity being at a fully unexpected and unhoped level.

Lastly, for some compounds, besides the above mentioned properties, an antiinflammatory activity is found.

To sum up, the compounds of the present invention show a composite activity, by which they are very promosing for the cases in which the main activity must be combined with a specific secundary action.

The compounds of the invention can be formulated for the oral administration, as tablets, capsules, pills, suspensions and syrups, as well as in form of suppositories for rectal use and in other forms for the topic use, such as ointments, creams and the like.

There are further foreseable and foreseen the time delayed formulations. In the pharmaceutical preparations, the compounds of the present invention shall be combined with suitable excipients and vehicles, according to the well known techniques for the preparation of the above types of compositions.

I claim:

1. Compound of the formula

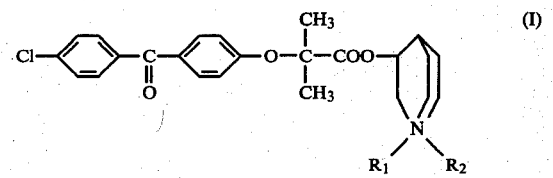

wherein $R_1$ is hydrogen or methyl and $R_2$ is hydrogen, chlorine, bromine or a radical of an acid selected from the group consisting of oleic, pivalic, nicotinic, clofibric, 3-pyridineacetic and theophyllineacetic acids.

2. 3-hydroxy-quinuclidine ester of p-(4-chlorobenzoyl)-phenoxy-isobutyric acid, according to claim 1.

3. 3-hydroxy-quinuclidine ester of p-(4-chlorobenzoyl)-phenoxy-isobutyric acid hydrochloride, according to claim 1.

4. 3-hydroxy-quinuclidine ester of p-(4-chlorobenzoyl)-phenoxy-isobutyric acid oleate, according to claim 1.

5. 3-hydroxy-quinuclidine ester of p-(4-chlorobenzoyl)-phenoxy-isobutyric acid methylbromide, according to claim 1.

6. 3-hydroxy-quinuclidine ester of p-(4-chlorobenzoyl)-phenoxy-isobutyric acid pivalate, according to claim 1.

7. 3-hydroxy-quinuclidine ester of p-(4-chlorobenzoyl)-phenoxy-isobutyric acid nicotinate, according to claim 1.

8. 3-hydroxy-quinuclidine ester of p-(4-chlorobenzoyl)-phenoxy-isobutyric acid, clofibrate, according to claim 1.

9. 3-hydroxy-quinuclidine ester of p-(4-chlorobenzoyl)-phenoxy-isobutyric acid, pyridineacetate, according to claim 1.

10. 3-hydroxy-quinuclidine ester of p-(4-chlorobenzoyl)-phenoxy-isobutyric acid, theophyllineacetate, according to claim 1.

* * * * *